| United States Patent [19]
Katdare | [11] Patent Number: 4,639,458 |
| | [45] Date of Patent: Jan. 27, 1987 |

[54] TABLET AND FORMULATION

[75] Inventor: Ashok V. Katdare, Ambler, Pa.

[73] Assignee: Merck & Co., Inc., Rahway, N.J.

[21] Appl. No.: 693,071

[22] Filed: Jan. 22, 1985

[51] Int. Cl.$^4$ .......................... A61K 31/47; A61K 9/20
[52] U.S. Cl. ..................................... 514/311; 514/781;
514/960
[58] Field of Search .......... 514/960, 781, 311

[56] References Cited

U.S. PATENT DOCUMENTS

| Re. 29,077 | 12/1976 | Geller | 424/15 |
|---|---|---|---|
| 3,873,694 | 3/1975 | Kanig | 424/154 |
| 4,072,535 | 2/1978 | Short et al. | 106/210 |
| 4,097,606 | 6/1978 | Chavkin et al. | 514/960 |
| 4,293,539 | 10/1981 | Ludwig et al. | 424/19 |
| 4,369,172 | 1/1983 | Schor et al. | 424/19 |
| 4,370,313 | 1/1983 | Davies | 424/32 |
| 4,440,740 | 4/1984 | Fix et al. | 514/772 |
| 4,478,822 | 10/1984 | Haslam et al. | 424/78 |
| 4,517,179 | 5/1985 | Raghunathan | 514/259 |
| 4,522,818 | 6/1985 | Raghunathan | 514/155 |
| 4,530,928 | 7/1985 | Haslam et al. | 514/254 |
| 4,540,602 | 9/1985 | Motoyama et al. | 424/35 |

Primary Examiner—Shep K. Rose
Attorney, Agent, or Firm—Samuel B. Abrams; Hesna J. Pfeiffer; Julian S. Levitt

[57] ABSTRACT

A direct compression tablet formulation containing a non-hydrated quinoline carboxylic acid type antibacterial agent.

3 Claims, No Drawings

TABLET AND FORMULATION

BACKGROUND OF THE INVENTION

The invention is concerned with a direct compression quinoline carboxylic acid tablet which utilizes non-hydrated quinoline carboxylic acid.

Certain quinoline carboxylic acids are known orally active antibacterial agents. (see e.g. U.S. Pat. No. 4,146,719; U.S. Pat. No. 3,590,036; U.S. Pat. No. 4,292,317)

Norfloxacin is a particularly effective agent of this class and has the formula

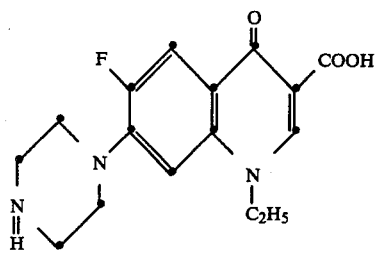

Its formulation into a tablet oral dosage form is disclosed in Italian patent application No. 20764A/79; this formulation requires that it contain about 2% to about 15% water to permit preparation of a tablet containing the minimal amount of inert ingredients carriers etc. and having suitable dissolution, disintegration and bioavailability characteristics. This water is added to the formulation ingredients prior to compression into a tablet.

A tablet formulation has been discovered which requires no hydration, i.e. no addition of water prior to compression and which contains lesser amounts of inert ingredients than the prior art formulation, while maintaining equivalent dissolution, disintegration, bioavailability and strength properties of the tablet prepared therefrom. The tablet formulation may be equally useful for other quinoline carboxylic acid type agents.

SUMMARY OF THE INVENTION

A direct compression tablet and a non-hydrated formulation for its preparation containing quinoline carboxylic acid antibacterial.

DESCRIPTION OF THE INVENTION

An embodiment of the invention is a direct compression tablet formulation containing quinoline carboxylic acid antibacterial agent.

Examples of useful quinoline carboxylic acids are norfloxacin, ciprofloxacin, enoxacin, ofloxacin, cinoxacin, nalidixic acid, rosoxacin, oxolinic acid, flunaquine, amifloxacin, pipemidic acid, pefloxacin and the like. A preferred quinoline carboxylic acid is norfloxacin.

The present formulation comprises a blend of said antibacterial agent and minimal amounts of other processing aids with no water added. More specifically, the processing aids are a disintegrant, a filler/binder and a lubricant, with a colorant being optionally added and the antibacterial agent is norfloxacin.

This formulation is directly compressed into a tablet which is generally film coated, preferably using a conventional aqueous coating system. The film former is typically modified cellulose e.g. hydroxypropylcellulose and/or hydroxypropylmethylcellulose.

Following are the compositions of illustrative tablet formulations containing 200 and 400 mg of an antibacterial agent (norfloxacin).

DIRECT COMPRESSION FORMULATION

| Component | A mg/tablet | B mg/tablet | Approx. Weight % |
|---|---|---|---|
| 1. Norfloxacin | 200 | 400 | 80 |
| 2. Microcrystalline Cellulose NF | 42.8 | 85.5 | 17 |
| 3. Croscarmellose Sodium NF | 5.0 | 10.10 | 2 |
| 4. Magnesium Stearate NF | 2.2 | 4.4 | 0.9 |
| 5. Red Ferric Oxide NF | <0.1 | <0.19 | <0.04 |

The tablet is prepared by mixing the formulation ingredients with no hydration i.e. no water is added, prior to direct compression. This mixture of ingredients is thus substantially dry, that is, it will contain less than about 2% or preferably less than about 1% water. The tablet may be optionally film coated preferably using a water based system.

The prior art formulation described in the above-cited Italian patent application requires addition of at least about 2% up to about 15% water to the tablet formulation prior to compression. The specific formulations disclosed in the examples of the Italian application show that tablet ingredients (norfloxacin is the active ingredient) are first subjected to a granulation followed by addition of water (6% in Example 7, 8.2%-Example 2, 8%-Example 3, and 4) prior to compression. The present formulation also provides a processing advantage since it requires only blending of the ingredients without granulation or addition of water prior to compression. The elimination of the granulation operation also eliminates the use of a solvent (e.g., ethanol), and its attendant evaporation which could present environmental concerns.

The dissolution rate, disintegration times and breaking resistance (tablet strength) and active ingredient bioavailability of tablets of the A and B formulations and of tablets formulated according to the Italian patent directions were found to be substantially equivalent. In each instance the tablets (A and B or Italian) were additionally film coated using conventional tablet film coating systems (aqueous for A and B and solvent for Italian both utilizing a modified cellulose film former). Each tablet formulation also contained a trace (<0.04% by weight) of a colorant.

The strength and dissolution data are tabulated below:

COMPARATIVE PHYSICAL PROPERTIES OF TABLETS

| Tablet Formulation (Norfloxacin, Mg) | Breaking[1] Strength (Kps) | Dissolution %[2] at 10, 20, 30 minutes | | |
|---|---|---|---|---|
| A (200) | 9.57 ± .54 | 104, | 101, | 101 |
| | 9.94 ± .26 | 101, | 100, | 101 |
| | 11.03 ± .32 | 103, | 103, | 108 |
| | 14.25 ± .33 | 109, | 111, | 110 |
| Italian Application (200) | 10.23 ± .35 | 99, | 114, | 113 |
| | 11.23 ± .18 | 72, | 110, | 112 |
| | 12.95 ± .26 | 78, | 111, | 114 |
| B (400) | 11.88 ± .33 | 97, | 104, | 102 |
| | 12.45 | 103, | 103, | 100 |
| | 14.28 | NA, | 101, | 100 |
| | 17.28 | 97, | 98, | 96 |
| | 18.6 | NA, | 95, | 100 |
| | 20.0 | 67, | 102, | 102 |

| Tablet Formulation (Norfloxacin, Mg) | Breaking[1] Strength (Kps) | Dissolution %[2] at 10, 20, 30 minutes | | |
| --- | --- | --- | --- | --- |
| Italian Application (400) | 11.80 ± .57 | 101, | 102, | 102 |
| | 13.28 ± .30 | 96, | 101, | 102 |
| | 16.18 ± .35 | 90, | 100, | 103 |
| | 17.20 ± .20 | 92, | 98, | 103 |
| | 19.15 ± .44 | 83, | 100, | 102 |
| | 20 | 76, | 97, | 100 |

[1]Schleuniger 2E tester
[2]Using USP apparatus II, paddles at 50 RPM

The data show that the physical properties of the Italian application and present formulations are substantially equivalent.

While only tablets containing 200 and 400 mg of the active ingredient (antibacterial agent) are shown, tablets containing more or less of the active ingredient can be prepared as needed.

Claims to the invention follow.

What is claimed is:

1. A composition containing by weight, about 80–85% norfloxacin, about 13.5–18.5% microcrystallin cellulose, about 0.5–2% magnesium stearate, and about 1–4.5% croscarmellose sodium.

2. The composition of claim 1 containing a trace amount of colorant.

3. A tablet prepared from the composition of claim 1 or 2.

* * * * *